(12) United States Patent
Kühnl et al.

(10) Patent No.: US 8,940,230 B2
(45) Date of Patent: Jan. 27, 2015

(54) CELL FOR CONDUCTING ELECTROCHEMILUMINESCENCE MEASUREMENTS

(75) Inventors: Michael Kühnl, München (DE); Herbert Buschek, Weilheim (DE); Reinhold Krämer, Peissenberg (DE); Petra Ickler, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1001 days.

(21) Appl. No.: 11/895,271

(22) Filed: Aug. 23, 2007

(65) Prior Publication Data
US 2008/0047332 A1 Feb. 28, 2008

(30) Foreign Application Priority Data

Aug. 25, 2006 (EP) .................................. 06017810

(51) Int. Cl.
 *G01N 21/76* (2006.01)
 *G01N 21/00* (2006.01)
 *G01N 21/66* (2006.01)
 *G01N 21/05* (2006.01)

(52) U.S. Cl.
 CPC ................ *G01N 21/76* (2013.01); *G01N 21/66* (2013.01); *G01N 21/05* (2013.01)
 USPC .... 422/52; 422/82.01; 422/82.05; 422/82.08; 250/361 C; 436/164; 436/172

(58) Field of Classification Search
 USPC ..................... 422/52, 82.05; 250/361, 361 C; 436/164–172
 See application file for complete search history.

(56) References Cited

U.S. PATENT DOCUMENTS

| | | | |
|---|---|---|---|
| 5,538,687 | A | 7/1996 | Kotzan et al. |
| 5,746,974 | A | 5/1998 | Massey et al. |
| 6,599,473 | B1 | 7/2003 | Egger et al. |

(Continued)

FOREIGN PATENT DOCUMENTS

| | | |
|---|---|---|
| DE | 43 43 942 A1 | 8/1999 |
| DE | 198 03 528 A1 | 8/1999 |

(Continued)

OTHER PUBLICATIONS

Song et al., A microfluidic system for controlling reaction networks in time, 2003 Wiley-VCH, Angew. Chem. Int. Ed. 2003, 42, No. 7, pp. 767-772.*

*Primary Examiner* — In Suk Bullock
*Assistant Examiner* — Robert Eom
(74) *Attorney, Agent, or Firm* — Dinsmore & Shohl LLP

(57) ABSTRACT

A cell for conducting electrochemiluminescence measurements is disclosed. The cell in one embodiment provides a measurement cell housing having a cavity, a fluid inlet channel for inducing fluid into the cavity and a fluid outlet channel for discharging fluid from the cavity at axial ends. The cell also provides at least one working electrode and a counter electrode on or in the cavity, and an optical viewing element for observing electrochemiluminescence effects in the cavity, wherein the fluid inlet channel has an at least approximately continuous curved course in a transition area to the cavity so that the fluid inlet channel at its end which is joined to the cavity is shaped in such a manner as to constitute a continuous course of the transition between the fluid inlet channel and the cavity to generate a largely steady flow profile when inducing fluid into the measurement cell cavity.

13 Claims, 1 Drawing Sheet

(56) References Cited

U.S. PATENT DOCUMENTS

2003/0175947 A1 * 9/2003 Liu et al. .................. 435/288.5

FOREIGN PATENT DOCUMENTS

| | | |
|---|---|---|
| JP | 09189662 A2 | 7/1997 |
| JP | 10332593 A2 | 7/1997 |
| JP | 2002502035 | 1/2002 |
| JP | 2005241522 | 9/2005 |
| WO | 8910551 A1 | 11/1989 |
| WO | 8910552 A1 | 11/1989 |
| WO | 9011511 A1 | 10/1990 |

* cited by examiner

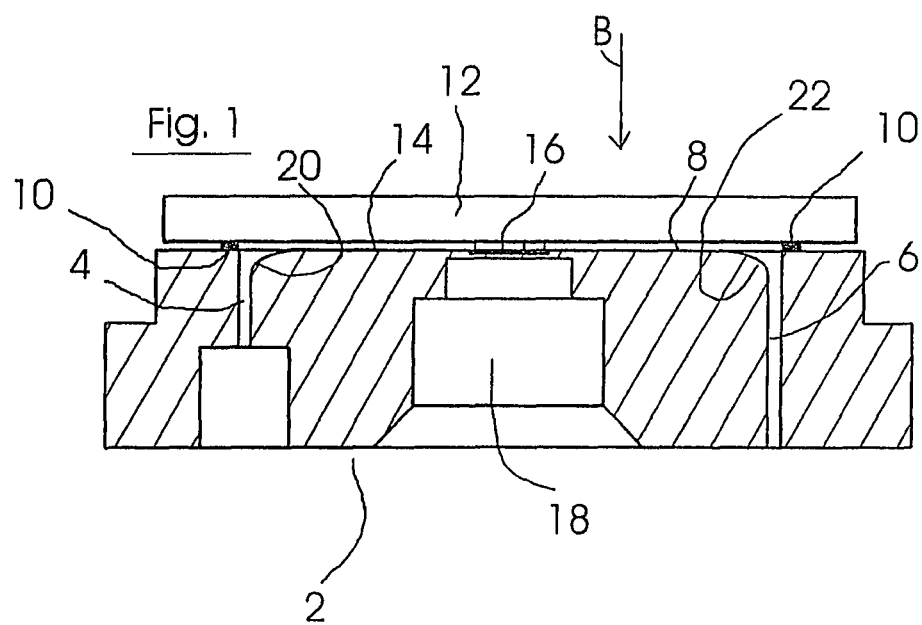
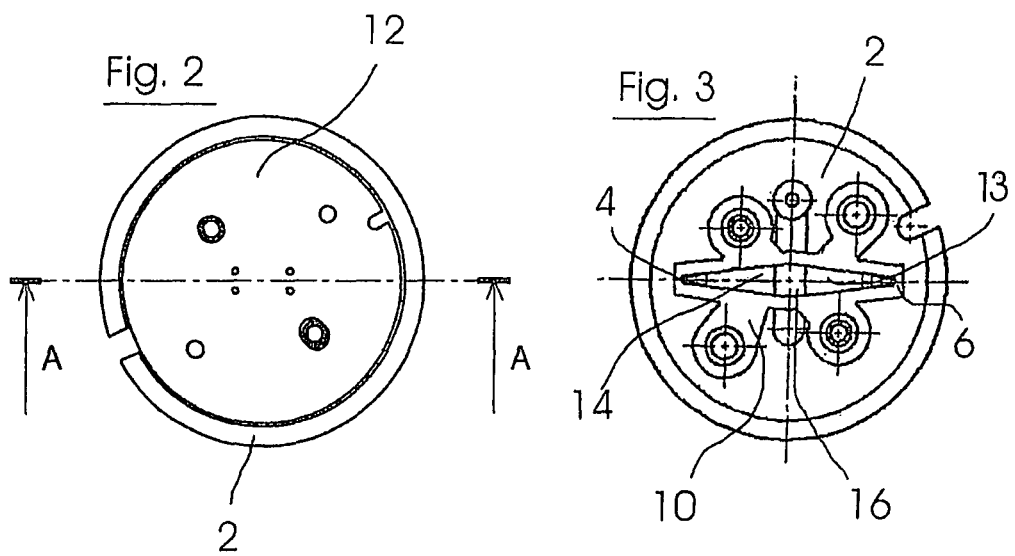

US 8,940,230 B2

CELL FOR CONDUCTING ELECTROCHEMILUMINESCENCE MEASUREMENTS

FIELD OF THE INVENTION

The present invention relates generally electrochemiluminescence measurements, and in particular to a cell for conducting electrochemiluminescence measurements for analysing samples providing a measurement cell housing having a measurement cell cavity in the form of an oblong channel, a fluid inlet channel extending transversely to the longitudinal direction of the measurement cell cavity toward the latter for inducing fluid into the measurement cell cavity and a fluid outlet channel for discharging fluid from the measurement cell cavity at the axial ends of the measurement cell cavity, at least one working electrode and a counter electrode on or in the measurement cell cavity and an optical viewing element in the measurement cell housing for observing electrochemiluminescence signals in the measurement cell cavity.

BACKGROUND OF THE INVENTION

Measurement cells of the kind and methods for analysing samples by means of electrochemiluminescence tests, particularly immunoassay tests using such measurement cells, are, for example known from DE 43 42 942 A1, DE 198 03 528 A1, WO89/10551 A1 and WO90/11511 so that for the understanding of the basic technology concerning the subject-matter of the present invention reference is made to these publications.

When analysing a liquid sample by means of electrochemiluminescence tests usually the concentration of a substance (analyte) contained in the sample liquid is to be determined. In the medical field particularly the analysis of body fluids like blood, urine, saliva etc. is of great importance, in view of analytes contained therein, as for example antibodies, antigens, hormones etc.

A typical measurement process in such tests comprises the multiple exchange of liquids and/or mixtures in the measurement cell. Hence, during a typical measurement, a first mixture is induced into the cleaned measurement cell through the fluid inlet channel into the measurement cell cavity. The first mixture is an incubate of the sample, reagents and magnetic particles. In the present considered tests the complex-molecules, which are marked with an electrochemiluminescence marker substance and are characteristic for the analysis, are fixed to these magnetic particles. Such a fixation is effected by a pair of specific biochemical binding partners, whereby particularly the pair streptavidin-biotin proved of value. The magnetic particles are for example coated with streptavidin-polymer, whereas biotin is bound to the complex-molecules.

In known measurement cells the magnetic particles are trapped to the surface of the working electrode together with the marked complex bound thereto in the magnetic field of a magnet arranged close to the working electrode. This may be effected during the continuous flow of the first mixture, whereby incubation fluid discharges from the measurement cell cavity through the fluid outlet channel. The accumulation of the magnetic particles on the working electrodes while discharging incubation fluid is called bound free separation.

After trapping the magnetic particles, a measurement reagent may be induced into the cell in a next step, whereby the magnetic particles are washed by this measurement reagent. This step of washing is to remove unbound components from the working electrode which potentially interfere with the electrochemical reaction.

Thereafter the electrochemiluminescence reaction is triggered by application of an electric potential to the working electrode, whereby the intensity of the luminescence light is detected by means of a photosensor and may be evaluated as a measure for the concentration of the marked magnetic particles on the surface of the working electrode, whereby this concentration again serves as a measure for the concentration of the analyte in the sample.

After the electrochemiluminescence measurement the cell usually is rinsed with a cleaning fluid, which in a further step may be discharged with the measurement reagent in order to condition the cell for the next measurement.

It is essential for the quality of the measurement that the above-mentioned washing step is efficient, so that in the mixture of measurement reagent and magnetic particles, separated from the incubate, the least possible amount of interfering components, as for example sample components, is contained. Such interfering components could cause changes of the measurement signal. Such measurement interferences are also called matrix effects. If the above-mentioned washing step is executed too violently, this may, however, also lead to negative effects, if—for example—due to too large flow velocities, turbulences, etc., magnetic particles are removed from their position on the working electrode.

In known measurement cells the fluid inlet channel and the fluid outlet channel meet the measurement cell cavity orthogonally to the longitudinal direction of the oblong measurement cell cavity, so that, when fluid is passed through the measurement cell, the respective fluid flow is abruptly deflected by an angle of 90° when being induced into the measurement cell cavity—and finally again by an angle of 90° when being discharged from the measurement cell cavity. Such a geometry of the fluid channels was established due to reasons of construction and production, and hitherto has been considered to be well suited for an optimal operation of the measurement cell.

In known measurement cells the housing thereof comprises a base block which is interspersed by the fluid inlet channel and the fluid outlet channel and delimits the measurement cell cavity by one of its lateral surfaces, with the working electrode being provided on the peripheral face of the measurement cell cavity. The fluid channels penetrate the base block and extend orthogonally with respect to the plane of the peripheral face of the measurement cell cavity of the base block. A spacer acting as a washer and having a central clearance is seated on the base block and forms the limit of the side wall of the measurement cell cavity with its internal contour. An acrylic glass panel is positioned on the spacer-washer as an optical window, on which the counter electrode is provided opposite to the working electrode.

SUMMARY OF THE INVENTION

It is against the above background that the present invention provides a measurement cell of the above-mentioned kind by which matrix effects of the electrochemiluminescence may be prevented more efficiently than in the known generic measurement cells. Accordingly, in one embodiment, the present invention provides an improved measurement cell, particularly adapted to analyse samples by means of electrochemiluminescence binding reaction tests.

The present invention discloses that in a measurement cell comprising the above-mentioned features the fluid inlet channel has an at least approximately continuous curved course in the transition area to the measurement cell cavity so that the fluid inlet channel at its end which is joined to the measurement cell cavity is shaped in such a manner as to constitute a continuous course of the transition between the fluid inlet channel and the measurement cell cavity to generate a nearly continuous steady flow profile when inducing fluid into the measurement cell cavity.

The inventors have realized that by influencing the flow performance in the measurement cell cavity, particularly the bound free separation and the washing step, advancing the luminescence measurement step, may be executed more efficiently and at the same time gentler for the accumulation of magnetic particles and the marked complexes bound thereto, trapped on the working electrode. Tests have shown that a steady and relatively slow flow during the bound free and the washing step until the luminescence measurement takes place involves the best results concerning the suppression of the mentioned matrix effects. The inventors moreover realized that the flow performance in the measurement cell cavity may also be influenced in the range of the working electrode by geometrically constructive measures at the transition from the fluid inlet channel to the measurement cell cavity, and may be optimized as to homogeneity, by constructing the fluid inlet channel at its joining end in such a manner as to discharge into the measurement cell cavity by allowing a continuous flow at the transition to the measurement cell cavity.

Geometrical arrangements of the fluid inlet channel at its transition to the measurement cell cavity is chosen, which avoid abrupt deflections of the fluid flow, when induced into the measurement cell cavity.

In one embodiment, the fluid outlet channel is connected with a continuous and steady course to the measurement cell cavity, for example by having an at least approximately steadily curved course in the transitional region toward the measurement cell cavity, or leading away therefrom in longitudinal direction or, if required, at a small angle with respect to the longitudinal direction of the measurement cell cavity.

In one embodiment, the measurement cell housing comprises a base block interspersed by the fluid inlet channel and the fluid outlet channel and limiting the measurement cell cavity with one of its lateral surfaces, with the working electrode being provided on the peripheral face of the measurement cell cavity.

According to another embodiment of the measurement cell, the fluid inlet channel and the fluid outlet channel extend at least approximately orthogonally to the plane of the peripheral face of the measurement cell cavity in the base block, leading into the measurement cell cavity at the peripheral face of the measurement cell cavity at the axial ends of the longitudinal measurement cell cavity.

In another embodiment, a spacer, acting as a seal and having a central clearance, is seated on the peripheral face of the measurement cell cavity. The spacer has an internal contour laterally limiting the measurement cell cavity. In still another embodiment, a cover or panel comprising or acting as an optical window is seated on the spacer and is fixed to the base block, and in yet another embodiment, is directly screwed therewith. As an alternative, a light sensor could be provided instead of the window as a viewing element.

According to another embodiment of the measurement cell, the base block comprises a hollow space for accommodating a magnet on that side of the working electrode facing away from the measurement cell cavity.

These and other features and advantages of the various embodiments of the measurement cell according to the present invention will be more fully understood from the following detailed description of the various embodiments of the present invention taken together with the accompanying drawings briefly described hereinafter.

BRIEF DESCRIPTION OF THE DRAWINGS

FIG. 1 is a sectional view of a measurement cell embodiment according to the present invention with the section plane characterized at A-A in FIG. 2.

FIG. 2 shows the measurement cell of FIG. 1 in front view from a viewing direction indicated with arrow B in FIG. 1.

FIG. 3 shows a front view of the measurement cell of FIG. 2 with a removed window cover.

DETAILED DESCRIPTION

Reference will now be made in detail to several embodiments of a cell for conducting electrochemiluminescence measurements for analysing samples according to the present invention that are illustrated in the accompanying drawings. These embodiments are set forth for the purpose of illustrating and aiding in the understanding of the invention, and are not to be construed as limiting.

The designation of particular characteristics by numbers is used consistently in all the figures, unless indicated to the contrary. The figures are not to a uniform scale. However, within the individual figures, the proportions of the individual shape-describing elements (distances, angles, radii, contours) are in each case reproduced accurately with respect to one another and correspond to an illustrative embodiment.

According to FIG. 1 a measurement cell, generally indicated by symbol 1, comprises a base block 2, made in one embodiment of a non conducting material, which is interspersed with channels 4 and 6. The base block 2 comprises a peripheral face 8 of the measurement cell cavity on which a seal element and/or spacer element 10 is seated, the contour of which is shown in FIG. 3. The seal and/or spacer element 10 acts as a spacer for a cover 12 made of acrylic glass or the like, supported thereon, which serves as an optical viewing element for an external photosensor for luminescence detection.

The window cover 12 in one embodiment is directly screwed onto the base block 2 by means of screws (not shown in the figures). The screws also penetrate the seal and/or spacer element 10 acting as spacer between the window cover 12 and the base block 2 (cf. the screw hole pattern in FIGS. 2 and 3). In other embodiments, any conventional means of mounting the window cover 12 onto the base block 2 may be used.

The sealing and/or spacer element 10 has a central clearance 13 (cf. FIG. 3), the inner marginal contour thereof defining the longitudinal, approximately rhombic measurement cell cavity 14 of the example, which for the rest is delimited by the peripheral face 8 of the base block 2 and the window cover 12. The working electrode 16 is embedded in the peripheral face 8 of the measurement cell cavity in the base block 2. The counter electrode is located (not shown in the figures) at the window cover 12 opposite said working electrode 16. Further, a hollow space 18 is provided in the base block 2 on that side of the working electrode 16 facing away from the window cover 12, said hollow space 18 accommodating the magnet for trapping the magnetic particles during the bound free separation step.

As can be seen in FIG. 1, the channels 4, 6 lead into the measurement cell cavity 14 near the axial ends thereof, said channels 4, 6 having a continuously curved course, visible at 20, 22 in the transitional region to the measurement cell cavity 14, in order to generate a rather steady flow profile when inducing fluid into the measurement cell cavity and to provide for a smooth discharge of the fluid from the cavity 14 through the fluid outlet channel 6.

Such a measurement cell allows an efficient exchange of fluids and/or fluid mixtures in the measurement cell cavity 14 and, if required, a steady flushing of the measurement cell cavity 14 with fluids and/or fluid mixtures, particularly washing fluids so that a rather purified preparation of the accumulation of magnetic particles on the working electrode 16 and hence a suppression of matrix effects is possible in an easy manner.

Further, the function of the measurement cell of the invention is more tolerant in view of fabrication variances of its components.

Although the various embodiments of the present invention have been described using specific terms, such description is for illustrative purposes only, and it is to be understood that changes and variations may be made without departing from the spirit or scope of the following claims.

What is claimed is:

1. Measurement cell for conducting electrochemiluminescence measurements, comprising:
   a measurement cell housing having a measurement cell cavity in the form of an oblong channel, a fluid inlet channel extending transversely to the longitudinal direction of the measurement cell cavity toward the latter for inducing fluid into the measurement cell cavity, a fluid outlet channel for discharging fluid from said measurement cell cavity, at least one working electrode, and a counter electrode on or in said measurement cell cavity; and
   an optical viewing element in said measurement cell housing for observing electrochemiluminescence effects in said measurement cell cavity,
   wherein the fluid inlet channel has an at least approximately continuous curved course in the transition area to the measurement cell cavity.

2. The measurement cell according to claim 1, wherein the fluid outlet channel is connected to the measurement cell cavity with a continuous course.

3. The measurement cell according to claim 1, wherein the fluid outlet channel extends transversely to the longitudinal direction of the measurement cell cavity and has an at least approximately continuously curved course in the transition area to the measurement cell cavity.

4. The measurement cell according to claim 1, wherein the fluid outlet channel leads away from the measurement cell cavity extending in longitudinal direction thereof.

5. The measurement cell according to claim 1, wherein the measurement cell housing comprises a base block, interspersed by the fluid inlet channel and the fluid outlet channel and delimiting the measurement cell cavity with one of its lateral surfaces, wherein the working electrode is provided on said peripheral face of said measurement cell cavity.

6. The measurement cell according to claim 5, wherein the fluid inlet channel and the fluid outlet channel extend at least approximately orthogonally with respect to the plane of the peripheral face of the measurement cell cavity of said base block in said base block and lead into the measurement cell cavity at said peripheral face of said measurement cell cavity.

7. The measurement cell according to claim 6, wherein a spacer is seated on the peripheral face of said base block and comprises an internal contour laterally delimiting said measurement cell cavity, wherein a cover, comprising or acting as an optical window, is supported on said spacer, said cover being screwed to said base block.

8. The measurement cell according to claim 6, wherein said base block comprises a hollow space for accommodating a magnet on that side of said working electrode facing away from said measurement cell cavity.

9. The measurement cell according to claim 5, characterized in that a spacer is seated on the peripheral face of said base block and comprises an internal contour laterally delimiting said measurement cell cavity, wherein a cover, comprising or acting as an optical window, is supported on said spacer, said cover being fixed to said base block.

10. The measurement cell according to claim 9, wherein said base block comprises a hollow space for accommodating a magnet on that side of said working electrode facing away from said measurement cell cavity.

11. The measurement cell according to claim 5, wherein said base block comprises a hollow space for accommodating a magnet on that side of said working electrode facing away from said measurement cell cavity.

12. The measurement cell according to claim 1, wherein the measurement cell housing comprises a base block, interspersed by the fluid inlet channel and the fluid outlet channel and delimiting the measurement cell cavity with one of its lateral surfaces, wherein the working electrode is provided on said peripheral face of said measurement cell cavity, and the fluid outlet channel extends transversely to the longitudinal direction of the measurement cell cavity and has an at least approximately continuously curved course in the transition area to the measurement cell cavity and leads away from the measurement cell cavity in a longitudinal direction extending therefrom.

13. A method for conducting electrochemiluminescence measurements for analysing samples which comprises utilizing the measurement cell according to claim 1.

* * * * *